United States Patent
Guth et al.

(12)

(10) Patent No.: US 6,300,504 B1
(45) Date of Patent: Oct. 9, 2001

(54) USE OF WATER-SOLUBLE/DISPERSIBLE REACTIVE DERIVATIVES OF POLYIMIDO COMPOUNDS FOR MODIFYING PROTEINACEOUS SUBSTRATES

(75) Inventors: Jacob J. Guth, Upper Black Eddy, PA (US); Samual A. Vona, Jr., Bound Brook, NJ (US); John S. Thomaides, Berkeley Heights, NJ (US); Paul M. Petersen, Princeton, NJ (US); Carmine Iovine, Bridgewater, NJ (US)

(73) Assignee: National Starch & Chemical Investment Holding Corp., Wilmington, DE (US)

( * ) Notice: Subject to any disclaimer, the term of this patent is extended or adjusted under 35 U.S.C. 154(b) by 0 days.

(21) Appl. No.: 09/218,847

(22) Filed: Dec. 22, 1998

(51) Int. Cl.⁷ .............................. A61K 7/11; A61K 31/74; C07D 207/40
(52) U.S. Cl. .................... 548/547; 548/546; 548/485; 548/486; 424/70.1; 424/70.2; 424/70.4; 424/70.6; 424/70.9; 424/70.11; 424/70.122; 424/70.13; 424/70.17; 424/78.03; 424/400; 424/401; 564/153
(58) Field of Search ................. 424/70.1, 70.2, 424/70.4, 70.6, 70.9, 70.11, 70.122, 70.13, 70.17, 78.03, 400, 401; 548/485, 486, 546, 547; 564/153

(56) References Cited

U.S. PATENT DOCUMENTS

| | | |
|---|---|---|
| 4,279,996 | 7/1981 | Yoshioka et al. ............. 435/69 |
| 4,314,808 | 2/1982 | Jacquet et al. ................ 8/405 |
| 4,363,797 | 12/1982 | Jacquet et al. ............... 424/70 |
| 4,735,797 | 4/1988 | Grollier et al. .............. 424/47 |
| 5,175,285 | * 12/1992 | Lehman et al. ............. 544/141 |
| 5,686,066 | * 11/1997 | Harada et al. ............. 424/70.14 |

FOREIGN PATENT DOCUMENTS

| | | |
|---|---|---|
| 78-12516 | 4/1978 | (FR) . |
| 8-258688 | 9/1996 | (JP) . |

OTHER PUBLICATIONS

Chemical Abstracts 127:39464v (Matsuzawa et al., 1997).

* cited by examiner

Primary Examiner—Jose' G. Dees
Assistant Examiner—K. E. Shelborne
(74) Attorney, Agent, or Firm—Richard R Muccino

(57) ABSTRACT

This invention relates to water-soluble/dispersible reactive imido and polyimido compounds, wherein the polyimido compounds may be selected from the group consisting of polysuccinimide compounds, polyglutimide compounds, and copolymers of thereof. The polyimido compounds comprise a water-solubilizing/dispersing moiety that provides water-solubility and/or water-dispersibility to the polyimido compound and preferably is derived from a nucleophilic moiety selected from the group consisting of amines, alcohols, phenols, thiols, and carboxylates. The present invention also pertains to a proteinaceous substrate to which the imido or polyimido compound has been covalently bonded and to a method for treating a proteinaceous substrate with the imido or polyimido compound.

37 Claims, No Drawings

USE OF WATER-SOLUBLE/DISPERSIBLE REACTIVE DERIVATIVES OF POLYIMIDO COMPOUNDS FOR MODIFYING PROTEINACEOUS SUBSTRATES

FIELD OF THE INVENTION

This invention relates to water-soluble/dispersible reactive imido and polyimido compounds, wherein the polyimido compounds may be selected from the group consisting of polysuccinimide compounds, polyglutimide compounds, and copolymers of thereof. The polyimido compounds comprise a water-solubilizing/dispersing moiety that provides water-solubility and/or water-dispersibility to the polyimido compound and preferably is derived from a nucleophilic moiety selected from the group consisting of amines, alcohols, phenols, thiols, and carboxylates. The present invention also pertains to a proteinaceous substrate to which the imido or polyimido compound has been covalently bonded and to a method for treating a proteinaceous substrate with the imido or polyimido compound.

BACKGROUND OF THE INVENTION

Hair is a proteinaceous substrate containing protein chains connected by sulfur-sulfur cross-linkages from cystine. When hair is bleached or permed, the cystine disulfide bonds are cleaved, typically with sodium thioglycolate, sodium sulfite, or some other disulfide bond-cleaving agent. The hair is then put into a curled or straightened state, whichever is desired, and the disulfide bonds are then allowed to reform. New sulfur-sulfur cross-linkages between the protein chains are formed thus locking the hair into the new array. In practice, not all of the disulfide bonds reform. This cleavage of the sulfur-sulfur cross-linkages results in a weakening of the hair making it more susceptible to breakage during combing and brushing. In addition, because perming formulations are generally very alkaline, some amide linkages in the protein chains are also cleaved resulting in a further weakening of the hair. Currently, there is no cosmetically acceptable method of improving strength by imparting additional cross-linkages to hair. Moreover, both the strength of the hair and the combing properties of the hair are adversely affected by the perming/bleaching process. Conventional treatments to improve the combing properties include various conditioning agents. However, because these conditioning agents do not covalently bond to hair, their conditioning effects are removed by washing and must be repeatedly applied. Improved shine and gloss, UV protection, anti-stat properties, anti-microbial protection, color, as well as many other improvements, which are desirable to intact and/or damaged hair, all suffer from a lack of permanence on hair and must be continually replenished.

While there are many disclosures that describe compositions useful for modifying proteinaceous substrates, none of the disclosures describe compositions that are entirely satisfactory. None of the disclosures describe the preparation of water-soluble or water-dispersible reactive polyimido compounds that can be covalently and permanently bonded to a proteinaceous substrate. The present invention provides such improved water-soluble or water-dispersible polyimido compounds, many of which, upon reaction, revert to biodegradable and environmentally friendly compounds.

SUMMARY OF THE INVENTION

This invention relates to a polyimido compound selected from the group consisting of polysuccinimide compounds represented by Formula (1):

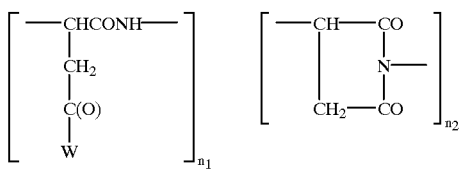

polyglutimide compounds represented by Formula (2);

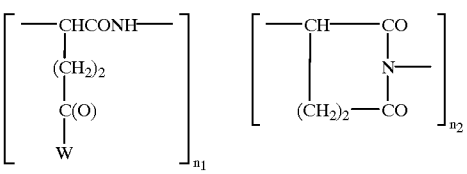

and copolymers of the polysuccinimide compounds represented by Formula (1) with the polyglutimide compounds represented by Formula (2), wherein W is a water-solubilizing/dispersing moiety that provides water-solubility and/or water-dispersibility to the polyimido compound; the ratio of $n_1$ to $n_2$ is from about 1:99 to about 99:1; and the molecular weight of the polyimido compound is from about 300 to about 1,000,000.

This invention also pertains to a proteinaceous substrate, having a polyimido compound covalently bonded to a portion thereof, wherein the polyimido compound is derived from a residue selected from the group consisting of polysuccinimide compounds represented by Formula (1):

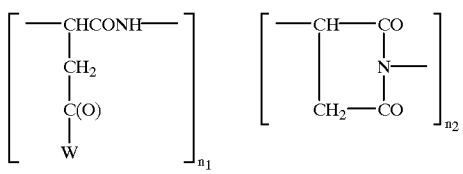

polyglutimide compounds represented by Formula (2);

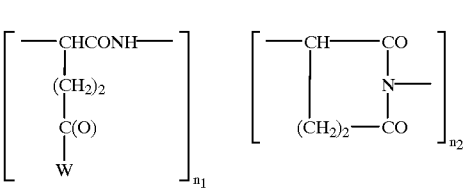

and copolymers of the polysuccinimide compounds represented by Formula (1) with the polyglutimide compounds represented by Formula (2); wherein W is a water-solubilizing/dispersing moiety that provides water-solubility and/or water-dispersibility to the polyimido compound; the ratio of $n_1$ to $n_2$ is from about 1:99 to about 99:1; and the molecular weight of the polyimido compound is from about 300 to about 1,000,000.

This invention also pertains to a method for treating a proteinaceous substrate which comprises the steps of:

(a) contacting a proteinaceous substrate with an aqueous solution/dispersion of an imido or polyimido compound at a pH value between about 4 and about 7 for a time sufficient to allow the imido or polyimido compound to be adsorbed/absorbed on or into the proteinaceous substrate; and (b) raising the pH value of the imido or polyimido compound adsorbed/absorbed on or into the proteinaceous substrate above about 7 for a time sufficient to allow the imido or polyimido compound to react with the proteinaceous substrate.

This invention also pertains to a method for treating a proteinaceous substrate which comprises the steps of:

(a) contacting a proteinaceous substrate with an aqueous solution of a polyimido compound at a pH value between about 4 and about 7 for a time sufficient to allow the polyimido compound to be adsorbed/absorbed on or into the proteinaceous substrate; and (b) raising the pH value of the polyimido compound adsorbed/absorbed on or into the proteinaceous substrate above about 7 for a time sufficient to allow the polyimido compound to react with the proteinaceous substrate;

wherein the polyimido compound is selected from the group consisting of polysuccinimide compounds represented by Formula (1):

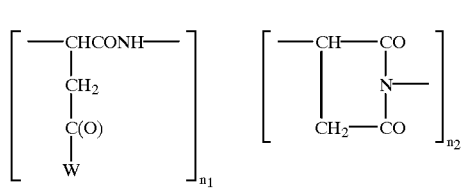

(1)

polyglutimide compounds represented by Formula (2);

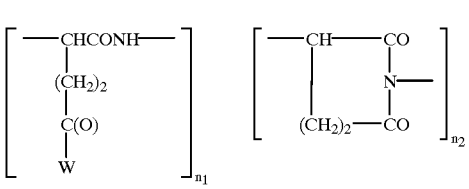

(2)

and copolymers of the polysuccinimide compounds represented by Formula (1) with the polyglutimide compounds represented by Formula (2), wherein W is a water-solubilizing/dispersing moiety that provides water-solubility and/or water-dispersibility to the polyimido compound; the ratio of $n_1$ to $n_2$ is from about 1:99 to about 99:1; and the molecular weight of the polyimido compound is from about 300 to about 1,000,000.

DETAILED DESCRIPTION OF THE INVENTION

The present invention is directed to water-soluble/dispersible reactive derivatives of polyimido compounds useful for modifying proteinaceous substrates such as hair, wool, skin, leather, silk, fur, felt, and nails. Applicants have found that reaction of a portion of the imide groups in the water-insoluble polysuccinimide (or polyglutimide) with a water-solubilizing/dispersing nucleophilic agent yields a water-soluble/dispersible polymer containing reactive sites at the remaining imide moieties. This water-soluble/dispersible polyimide, containing reactive imide moieties, is a water-soluble/dispersible acylating agent which can be covalently reacted with various nucleophilic groups present on the proteinaceous substrate to permanently impart changes to these substrates. Because of the unique and unexpected properties of the polyimido acylating agents of the present invention, the polyimido compounds can be used in applications to provide permanent modification of proteinaceous substrates such as hair and skin under aqueous conditions. In another embodiment, the polyimido acylating agents can be further reacted with a multifunctional nucleophilic agent to promote the development of cross-linked polymers to further modify the proteinaceous substrate. In yet another embodiment, the proteinaceous substrate may be bonded to a polyimido acylating agent having a water-solubilizing/dispersing moiety bearing a strong ionic charge which can electrostatically bind to moieties bearing the opposite charge. By priming the proteinaceous substrate with a highly charged polymer, one can modify the surface of the proteinaceous substrate to make it attract chemical moieties of the opposite charge and thereby impart a wide variety of beneficial properties to the proteinaceous substrate. Moreover, many of the polyimido compounds, upon reaction, revert to biodegradable and environmentally friendly compounds.

The present invention is also directed to a method for treating and/or modifying a proteinaceous substrate. The method comprises contacting a proteinaceous substrate with an aqueous solution of a polyimido compound at a pH value between about 4 and about 7 for a time sufficient to allow the polyimido compound to be adsorbed/absorbed on or into the proteinaceous substrate; followed by raising the pH value of the polyimido compound adsorbed/absorbed on or into the proteinaceous substrate above about 7 for a time sufficient to allow the polyimido compound to react with the proteinaceous substrate. The polyimido compound is best applied to the proteinaceous substrate in a two step, pH dependent method. The polyimido compound is first applied to the proteinaceous substrate at a pH value between about 4 and about 7, wherein the polyimido compound is relatively stable. Moreover, the aqueous solution of polyimido compound must be in contact for a time sufficient to allow the polyimido compound to be adsorbed/absorbed on or into the proteinaceous substrate. Thereafter, the pH value of the polyimido compound adsorbed/absorbed on or into the proteinaceous substrate is raised to above about 7 (preferably 8–10) for a time sufficient to allow the polyimido compound to react with the proteinaceous substrate. The pH value of the polyimido compound must be raised to above about 7 in order to deprotonate nucleophilic groups (amino groups, alcohol groups, phenolic groups, sulfhydryl groups, and carboxyl groups) present on the proteinaceous substrate which may then readily react with the reactive polyimido compound. The polyimido compound, at pH above about 7, must also be in contact with the proteinaceous substrate for a time sufficient to allow the polyimido compound to react with the proteinaceous substrate.

The time sufficient to allow the polyimido compound to be adsorbed/absorbed on or into the proteinaceous substrate and the time sufficient to allow the polyimido compound to react with the proteinaceous substrate are subject to such factors as the particular type of polyimido compound used, the water-solubilizing/dispersing moiety employed, the proteinaceous substrate employed, the temperature of the application, the resulting properties desired, as well as the particular application for which the compound may be used. In general, the time sufficient to allow the polyimido compound to be adsorbed/absorbed on or into the proteinaceous substrate and the time sufficient to allow the polyimido compound to react with the proteinaceous substrate may range from seconds to an hour.

Condensation of aspartic acid in the presence of an acid catalyst such as $H_3PO_4$ yields the water-insoluble polysuccinimide.

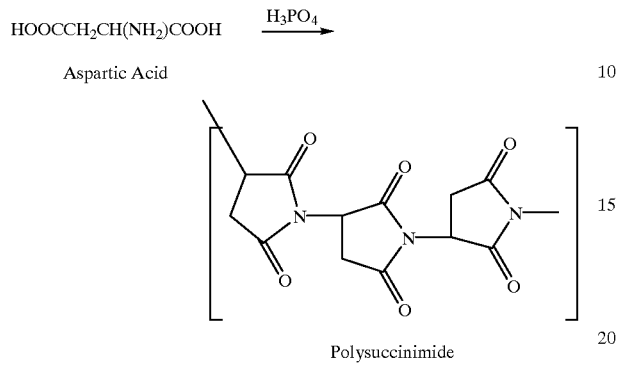

Partial reaction of the succinimide groups in polysuccinimide with a water-solubilizing/dispersing nucleophilic agent (W), usually carried out in an aprotic solvent such as dimethylsulfoxide, sulfolane, or dimethylformamide, results in the formation of a water-soluble/dispersible polymer containing reactive sites at the remaining succinimide moieties.

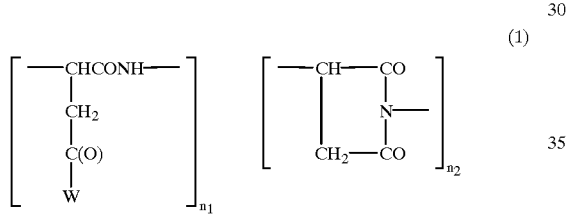

In accord with the present invention, a polyimido compound is provided which is selected from the group consisting of polysuccinimide compounds represented by Formula (1):

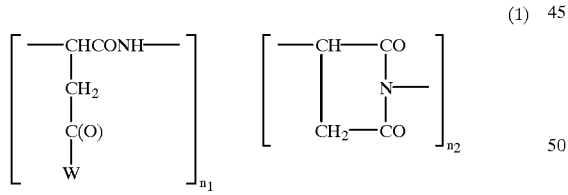

polyglutimide compounds represented by Formula (2);

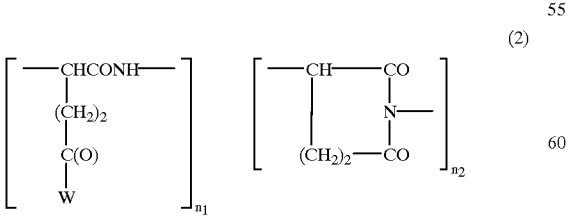

and copolymers of the polysuccinimide compounds represented by Formula (1) with the polyglutimide compounds represented by Formula (2), and mixtures thereof.

In Formula (1) and (2), W is a water-solubilizing/dispersing moiety that provides water-solubility and/or water-dispersibility to the polyimido compound. The water-solubilizing/dispersing moieties which may be employed in the present invention include all moieties which can covalently-react with the polyimido compound and provide water-solubility and/or water-dispersibility to the polyimido compound. In a preferred embodiment, the nucleophilic water-solubilizing/dispersing moieties may be derived from a nucleophilic moiety selected from the group consisting of amines, alcohols, phenols, thiols, and carboxylates. Preferably, W is the result of reacting a polyimido compound with an amine.

Preferred water-solubilizing/dispersing moieties may be selected from the group of nucleophiles consisting of:

(1) aminopolysaccharides preferably represented by the formula, $-N(R_1)-$ polysaccharide, wherein $R_1$ is hydrogen or lower alkyl ($C_1$ to $C_5$) and the number of units in the polysaccharide ranges from 1 to about 51. Substitution of from about 0.10 to about 0.80 equivalents of the polysaccharide, based on the available imide moieties, is generally required for solubilization. An example of a polyimido compound containing a maltodextrin aminopolysaccharide water-solubilizing/dispersing moiety is set out below.

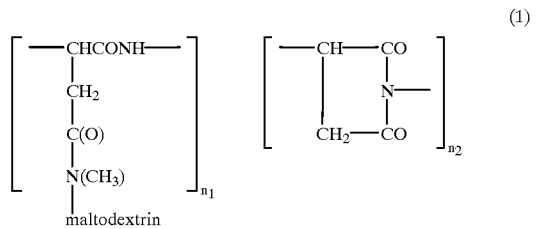

maltodextrin (2) amines containing quaternary ammonium salts preferably represented by the formula, $[-N(R_1)(CH_2)_{n3}N^+(CH_3)_3][A^-]$, wherein $R_1$ is hydrogen or lower alkyl ($C_1$ to $C_5$), $n_3$ is an integer from 1 to about 10, preferably from 1 to about 7, and A is a monovalent anion. Substitution of from about 0.10 to about 0.80 equivalents of the amino containing quaternary ammonium salt, based on the available imide moieties, is generally required for solubilization. An example of a polyimido compound containing an amino containing quatenary ammonium salt water-solubilizing/dispersing moiety is set out below.

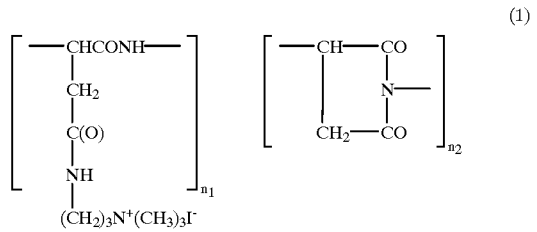

$(CH_2)_3N^+(CH_3)_3I^-$ (3) amines containing alcohols preferably represented by the formula, $-N(R_1)(CH_2)_{n4}OH$, wherein $R_1$ is hydrogen or lower alkyl ($C_1$ to $C_5$) and $n_4$ is an integer from 2 to about 10, preferably from 2 to about 7. Substitution of from about 0.10 to about 0.80 equivalents of the amino containing alcohol, based on available imide moieties, is generally required for solubilization. An example of a polyimido compound containing an amino containing alcohol water-solubilizing/dispersing moiety is set out below.

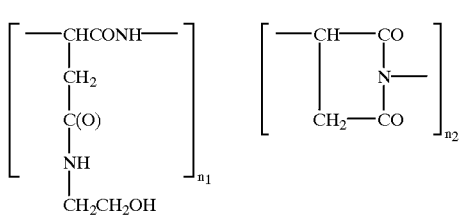
(1)

(4) amines containing polyalkoxylated alcohols preferably represented by the formula, $-N(R_1)CH(CH_3)CH_2-(OCHR_2CH_2)_{n5}-OCH_3$, wherein $R_1$ is hydrogen or lower alkyl ($C_1$ to $C_5$), $R_2$ may be hydrogen or methyl, and $n_5$ is an integer from 0 to about 50, preferably from 0 to about 35. Substitution of from about 0.10 to about 0.80 equivalents of the amino containing polyalkoxylated alcohol, based on available imide moieties, is generally required for solubilization.

(5) thiols containing alcohols preferably represented by the formula, $-S(CH_2)_{n6}OH$, wherein $n_6$ is an integer ranging from 2 to about 10 preferably from 3 to about 7. Substitution of from about 0.10 to about 0.80 equivalents of the thiol terminated compound, based on available imide moieties, is generally required for solubilization.

(6) alcohols containing ethers preferably represented by the formula, $-O(CH_2CH_2O)_{n7}OM$, wherein $n_7$ is an integer ranging from 0 to about 50, preferably from 0 to about 35, and M is an alkyl group containing from 1 to about 30 carbons, preferably from 1 to about 20. Substitution of from about 0.10 to about 0.80 equivalents of the hydroxyl terminated compound, based on available imide moieties, is generally required for solubilization.

(7) $-O^-X^+$, where X is selected from the group consisting of $H^+$, $Na^+$, $Li^+$, $NH_4^+$, $NH(CH_3)_3^+$; $NH_3(CH_2CH_2OH)^+$, $NH_2(CH_2CH_2OH)_2^+$, and $NH(CH_2CH_2OH)_3^+$; such as when the water-solubilizing/dispersing moiety is the result of ring opening of some of the imide groups with aqueous bases such as NaOH or $NH_4OH$. An example of a polyimido compound containing this type of water-solubilizing/dispersing moiety is set out below.

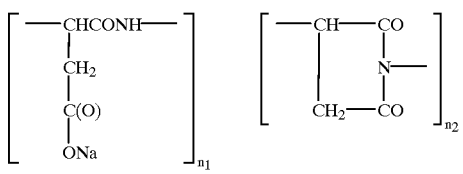
(1)

(8) $[-NH(CH_2)_3N^+(CH_3)_2CH_2COONa][A^-]$, $-N(CH_3)(CH_2)_2SO_3Na$ (N-methyltaurine), and $-NH(CH_2)_2SO_3Na$ (taurine), wherein A is a monovalent anion, including other anionic, amphoteric, or zwitterionic water-solubilizing groups.

Residues $n_1$ and $n_2$ in Formula (1) and (2) may be present in any order. The ratio of $n_1$ to $n_2$ is from about 1:99 to about 99:1; preferably from about and 5:95 to about 95:5, and more preferably from about 10:90 to about 90:10.

The molecular weight of the polyimido compounds is a matter of preference subject to such factors as the particular type of polyimido compound used, the type and charge characteristics of the water-solubilizing/dispersing moiety employed, the proteinaceous substrate employed, the resulting properties desired, as well as the particular application for which the compound may be used. In general, for internal modifications of proteinaceous substrates, the molecular weight of the polyimido compound will be under about 5000 and the water-solubilizing/dispersing moiety will be neutral or amphoteric (with a net neutral charge). In general, for external modifications of proteinaceous substrates, the molecular weight of the polyimido compound may be under or over 5000. However, polyimido compounds having a molecular weight over 5000 and cationic water-solubilizing/dispersing moieties will tend to remain on the surface rather than penetrate the proteinaceous substrate. However, techniques such as swelling the proteinaceous substrate may be employed to internally modify the proteinaceous substrate with polyimido compounds of higher molecular weight. In one embodiment, the molecular weight of the polyimido compound in Formula (1) and (2) is from about 300 to about 5000, preferably from about 1000 to about 4000; more preferably from about 1000 to about 3000; and most preferably from about 1000 to about 2000. In another embodiment, the molecular weight of the polyimido compound in Formula (1) and (2) is from about 5000 to about 1,000,000, preferably from about 5000 to about 500,000; more preferably from about 5000 to about 100,000; and most preferably from about 5000 to about 50,000.

In one preferred embodiment, the polyimido compound is a polysuccinimide represented by Formula (1). In another preferred embodiment, the polyimido compound is a polyglutimide represented by Formula (2). In yet another preferred embodiment, the polyimido compound is a copolymer of the polysuccinimide represented by Formula (1) (before derivatization) with the polyglutimide represented by Formula (2) (before derivatization).

The scope of the present invention need not be limited to polyimido compounds such as polysuccinimide compounds, polyglutimide compounds, and copolymers thereof, but may also include imido compounds. The imido compounds may be water-soluble or water-dispersible natural or synthetic polymers to which reactive imide moieties such as succinimide, glutimide, or phthalimide groups have been appended or, into the backbones of which, reactive imide moieties have been incorporated to form imido compounds. These imido compounds can be prepared by copolymerization reactions or by polymer modification reactions.

In a specific embodiment, the present invention is directed to a method for treating a proteinaceous substrate which comprises the steps of:

(a) contacting a proteinaceous substrate with an aqueous solution/dispersion of an imido or polyimido compound at a pH value between about 4 and about 7 for a time sufficient to allow the imido or polyimido compound to be adsorbed/absorbed on or into the proteinaceous substrate; and (b) raising the pH value of the imido or polyimido compound adsorbed/absorbed on or into the proteinaceous substrate above about 7 for a time sufficient to allow the imido or polyimido compound to react with the proteinaceous substrate.

After reaction of a portion of the imide groups of the water-insoluble reactive polyimide, the water-soluble/dispersible polymer can now act as an acylating agent which can be covalently and permanently bonded to various nucleophilic groups present on a proteinaceous substrate. The proteinaceous substrates which may be employed in the present invention include all substrates containing nucleophilic groups which can covalently react with the polyimido acylating compounds. Suitable nucleophilic groups include amino groups, alcohol groups, phenolic groups, sulfhydryl groups, and carboxyl groups. Preferred proteinaceous substrates may be selected from the group consisting of hair, wool, skin, leather, silk, fur, felt, and nails.

The polyimido acylating compounds of the present invention may be employed in a pharmaceutically acceptable carrier to form therapeutic compositions. Suitable pharmaceutically acceptable carriers may be selected from the group consisting of water, water/alcohol mixtures, water/glycol mixtures, and mixtures thereof. Preferably, the pharmaceutically acceptable carrier is water.

The amount of polyimido compound present in the therapeutic compositions of the present invention is a therapeutically effective amount, that is, an amount effective to impart the modification properties desired. A therapeutically effective amount of polyimido compound is that amount of polyimido compound necessary for the inventive compound to provide the desired therapeutic effect. The exact amount of polyimido compound is a matter of preference subject to such factors as the particular type of polyimido compound, the molecular weight of the polyimido compound employed, the temperature of the application, the resulting properties desired, as well as the particular application for which the therapeutic composition may be used, i.e, substrate type, application, conditions, end-use. In a preferred embodiment, the polyimido compound in the pharmaceutically acceptable carrier is present in an amount from about 1% to about 70%, preferably from about 5% to about 65%, and more preferably from about 10% to about 60%, by weight.

In a specific embodiment, the present invention is directed to a proteinaceous substrate, having a polyimido compound covalently bonded to a portion thereof, wherein the polyimido compound is derived from a residue selected from the group consisting of polysuccinimide compounds represented by Formula (1):

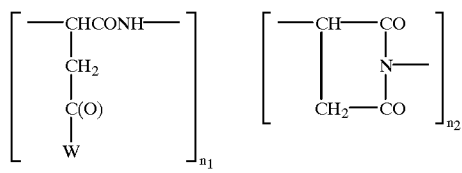

polyglutimide compounds represented by Formula (2);

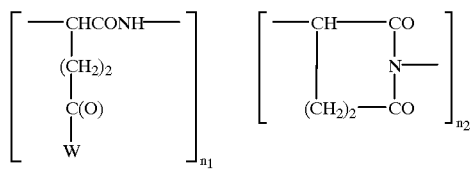

and copolymers of the polysuccinimide compounds represented by Formula (1) with the polyglutimide compounds represented by Formula (2); wherein W is a water-solubilizing/dispersing moiety that provides water-solubility and/or water-dispersibility to the polyimido compound; the ratio of $n_1$ to $n_2$ is from about 1:99 to about 99:1; and the molecular weight of the polyimido compound is from about 300 to about 1,000,000.

In another specific embodiment, the present invention is directed to a method for treating a proteinaceous substrate which comprises the steps of:

(a) contacting a proteinaceous substrate with an aqueous solution of a polyimido compound at a pH value between about 4 and about 7 for a time sufficient to allow the polyimido compound to be adsorbed/absorbed on or into the proteinaceous substrate; and (b) raising the pH value of the polyimido compound adsorbed/absorbed on or into the proteinaceous substrate above about 7 for a time sufficient to allow the polyimido compound to react with the proteinaceous substrate;

wherein the polyimido compound is selected from the group consisting of polysuccinimide compounds represented by Formula (1):

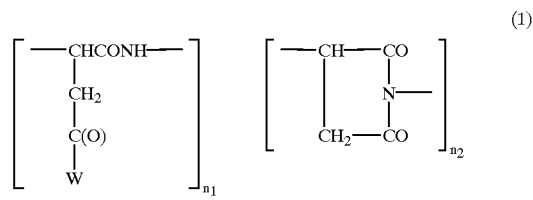

polyglutimide compounds represented by Formula (2);

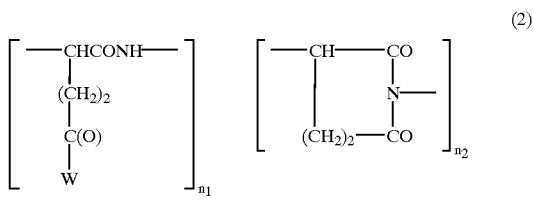

and copolymers of the polysuccinimide compounds represented by Formula (1) with the polyglutimide compounds represented by Formula (2), wherein W is a water-solubilizing dispersing moiety that provides water-solubility and/or water-dispersibility to the polyimido compound; the ratio of $n_1$ to $n_2$ is from about 1:99 to about 99:1; and the molecular weight of the polyimido compound is from about 300 to about 1,000,000.

In these latter two embodiments, suitable non-limiting proteinaceous substrates may be selected from the group consisting of hair, wool, skin, leather, silk, fur, felt, and nails. The polyimido compound may further be cross-linked to a multifunctional nucleophilic agent such as nucleophilic agents selected from the group consisting of 1,6-hexamethylenediamine, low-molecular weight polyethyleneimines, polyalkoxides, and polythiols. The water-solubilizing/dispersing moiety may further bear an ionic charge and be electrostatically bound to a moiety bearing the opposite charge such as those moieties selected from the group consisting of antimicrobals, ultraviolet chromophores, anionic dyes, anti-oxidants, fluorescing agents, brightening agents, shine and gloss enhancers, softening agents, and conditioning agents. In addition, the methods for treating a proteinaceous substrate may be carried out at elevated temperatures, such as from about 25° C. to about 55° C., to accelerate the reaction method.

Use of the Water-soluble/dispersible Polyimides Compounds for Modifying Hair

Hair may be reacted with a water-soluble/dispersible polyimide in order to impart a permanent benefit as set out below.

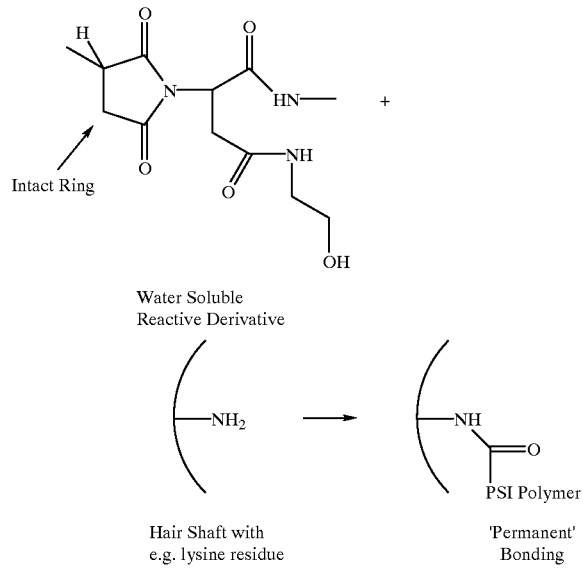

Internal Modification of Hair with Water-soluble/dispersible Polyimides

Reparation of Chemically Damaged Hair

Perming and bleaching of hair results in cleavage of the sulfur-sulfur cross-linkages connecting the protein chains resulting in a weakening of the hair. In addition, the perming formulations are generally very alkaline and may also cleave some amide linkages in the protein chains resulting in a further weakening of the hair. This effect is especially pronounced when the hair is wet. This chemically damaged hair can be repaired by imparting to the hair additional cross-linkages through reaction of a multifunctional acylating agent of the present invention with the various nucleophilic groups present in the hair. Nucleophilic moieties, such as the free amino groups present in the basic amino acids lysine, arginine, or histidine (which are naturally present in hair), terminal amino groups resulting from cleavage of amide bonds, sulfhydryl groups from the cleavage of cystine, and phenolic groups present in aromatic amino acids may all be employed in the acylation reaction.

Post Cross-linking to Further Repair Chemically Damaged Hair

In addition to cross-linking the protein chains in the hair with the polyimide acylating agents set out above, multifunctional nucleophilic agents such as 1, 6-hexamethylenediamine, low-molecular weight polyethyleneimines, polyalkoxides, and polythiols, can be added to the hair in order to react with the acylating agent and to promote the development of an internal polymeric network which can further strengthen the hair. Damaged hair may be treated with water-soluble/dispersible polyimides of various molecular weights ranging from 1000 to 4500, and preferably exhibiting a net neutral charge (due to the solubilizing group).

Non-Degradative Permanent Waving or Set

Perming or set can be imparted to hair without cleaving the disulfide bonds and without weakening of the hair by using a low molecular weight neutral charged water-soluble/dispersible polyimide to form new chemical cross-links between the polyimide and various nucleophiles (i.e., amino groups in lysine, terminal amino groups, phenoxide groups, etc). which exist within the hair fiber. Alternatively, additional cross-links can be formed to develop an internal polymeric structure by first allowing the polyimide to penetrate the hair and then following with the addition of multifunctional nucleophilic agents such as polyamines, polythiols, and the like. In one preferred embodiment, a water-soluble/dispersible polyimide of the present invention, having a molecular weight between approximately 300 and 5000, is applied to hair (which has been place in a curled array) at a pH between about 4 and about 7 and allowed to penetrate the hair. After a time sufficient to penetrate the hair, the hair is treated with a buffer solution having a pH 8–10 and a temperature between 20–55° C. In a more preferred embodiment, a water-soluble/dispersible polyimide, which is neutral in charge, and having a molecular weight between approximately 1000 and 4000 is used as above at a temperature between 30 and 55° C. In a most preferred embodiment, a water-soluble/dispersible polyimide, which is neutral in charge, and having a molecular weight between approximately 2000 and 3000 is used as above at a temperature between 35 and 45° C.

External Modification of Hair with Water-soluble/dispersible Polyimides

Reaction of a water-soluble/dispersible polyimide of the present invention can be confined to the exterior of the hair generally by controlling the molecular weight and the charge of the polyimide. A water-soluble/dispersible polysuccinimide of molecular weight>5000 can be applied to the hair at the appropriate pH, whereupon the pH is elevated, and the hair is heated to effect the covalent linkage with the polymer.

The Primer Approach

Intact hair is normally quite hydrophobic. However reaction of hair with a water-soluble/dispersible polyimide, especially one which is highly charged or in which the polymer will exhibit a charge after hydrolysis of residual imide moieties, will result in hair which has a much more hydrophilic surface. Hair normally has an overall negative charge because of the presence of high levels of aspartic acid and glutamic acid. Reaction of hair with a polyimide made water-soluble/dispersible by the presence of a large number of quaternary groups will impart an overall positive charge on the surface of the hair. An advantage of covalently binding a water-soluble/dispersible polyimide carrying a high positive charge to hair is that the positive charges on the polymer become a magnet for anionic species. By priming the hair with a positively charged polymer, such as the structure shown below, one can attract and bind anionic chemical moieties:

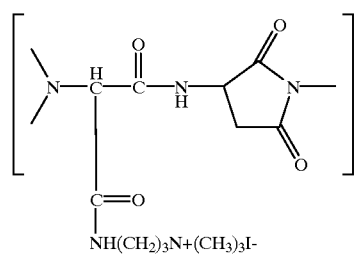

The primer approach may be used to impart a wide variety of beneficial properties to the hair by exposing the cationically modified hair to the appropriate anionic group (typically delivered from a shampoo, lotion, spray etc.), which would then become electrostatically bound to the polymer. The following are potential uses of this approach (a) Antimicrobials having an anionic charge, e.g., Triclosan, a phenolic can be bound to the surface of hair providing protection to the hair and the scalp from attack by microrganisms.
(b) UV chromophores, having anionic charge such as methoxycinnamic acid or para-aminobenzoic acid, can be bound to hair providing protection to the hair from UV light.
(c) Anionic dyes, such as tartrazine, can be bound to hair to provide color.
(d) Anti-oxidants, such as sodium ascorbate, can be bound to hair providing protection from oxidation to the hair and to its melanin.
(e) Fluorescing agents.
(f) Brightening agents.
(g) Shine and gloss enhancers.
(h) Softening agents.
(i) Conditioning agents.

Use of the Primer Approach to Impart Conditioning to Hair

Damaged hair, whether it is chemically damaged from a bleaching or perming process, from weathering, or from physical damage such as teasing or ratting, typically has very poor combing properties. A number of positively charged water-soluble/dispersible polyimides may be reacted onto the surface of damaged hair to attract conditioners. Ease of wet combing is viewed as an indication of "conditioned hair" . Results from experiments (described below) testing this idea clearly show that the highly positively charged polyimide having been covalently reacted to the hair, is then able to electrostatically bind the sodium lauryl sulfate, in which it is subsequently washed, to itself and in the process to the surface of the hair where it serves to lubricate the hair and to provide improved wet combing.

Use of the Water-soluble/dispersible Polyimido compounds for Modifying Skin

In principal, the same approach used to achieve external modification of hair can be used to modify the surface of the skin, i.e., either high molecular weight>5000 or positively charged water-soluble/dispersible polyimides would be used. The polyimide would be applied to the skin at a pH between 4 and 7, whereupon the pH of the skin would then be raised with a buffer to above about 7 and the temperature raised to between 35 and 45° C.

Use of the Water-soluble/dispersible Polyimido Compounds in Skin Care

The water-soluble/dispersible polyimido compounds of the present invention may be employed to protect skin from alkaline attack, such as from dishwashing liquids. A water-soluble/dispersible polyimido compound, such as the structure set out below or others in which the the solubilizing groups are present at a minimum concentration so that hydrolysis of the residual succinimide moieties would result in the maximum amount of aspartate residues present, may be employed to bind to the skin and exhibit maximum buffer capacity.

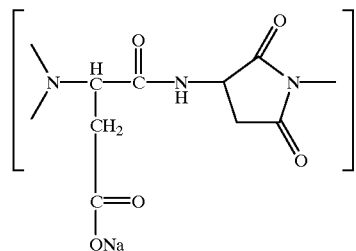

Use of the Primer Approach to Provide Benefit to Skin

As set out above for hair, a water-soluble/dispersible polyimide containing high levels of cationicity, such as is shown below, may be covalently bound to skin.

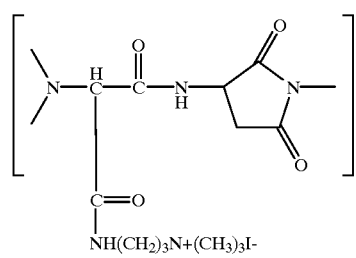

By using the primer approach, a wide variety of anionic species may be bound to the skin to provide numerous benefits. Anti-microbials and anti-fungals containing anionic groups would electrostatically bind to the positively charged primer and gradually release to the skin thereby giving longer lasting protection from various microorganisms. Ultra-violet chromophores, such as salts of methoxycinnamic acid and n, n-dimethylamino p-benzoic acid would bind thereby giving increased sun protection. Anionic Dyes could be applied to the skin treated with the positively charged polyimide thus providing body art having semi-permanence. Anionic conditioning agents, e.g., anionic silicones or salts of fatty acids, or sulfated hydrocarbons could be electrostatically bound to impart to the skin a conditioned feel. Reparative or rejuvenative agents such as salts of glycolic acid or hyaluronic acid could be bound to the skin and then gradually released over time.

The precise formulation of the therapeutic composition will vary depending upon the specific end use. Other ingredients may also be incorporated into the therapeutic compositions as dictated by the nature of the desired composition as well known by those having ordinary skill in the art. The therapeutic compositions are readily prepared using methods generally known in the therapeutic arts. Examples of additives traditionally used in therapeutics include emollients, rheology modifiers, fillers, humectants, thickeners, preservatives, dyes, and pigments, which may be employed in conventional amounts.

Illustrative examples of emollients include isopropyl myristate, isopropyl palmitate, isopropyl laurate, isopropyl stearate, glyceryl stearate, dioctyl adipate, cetyl oleate, PEG-7 glyceryl cocoate, PEG-15 glyceryl trioleate, polyglyceryl-3 dicaprate, polyglyceryl-3 laurate, cyclomethicone, and PPG-1-ceteth-1. Emollients are generally used in amounts from 2 to 30 parts by weight, preferably 3 to 20 parts.

Illustrative examples of thickeners include carbomer, carrageenan, salts of alginic acid, derivatives of chitosan, bentonite, casein, fumed silica, guar gum, gum tragacanth, hydroxy-ethylcellulose, locust bean gum, methylcellulose, polyacrylic acid salts (ammonium, potassium, sodium), polyvinyl alcohol, sodium carboxymethyl cellulose, and starches. When present, thickeners will be used in amounts up to about 10 parts by weight.

Illustrative examples of fillers include bentonites, calcium carbonate, calcium silicate, clay, mica, nut shell flours, silica, talc, uncooked starches, and wood flour. When present, fillers will be used in amounts up to about 20 parts by weight.

Illustrative examples of humectants include glucamine, PCA, glucuronic acid, polyglycerin-4, diethylene glycol, glycerine, hexylene glycol, propylene glycol, sorbitol, sucrose, and urea. When present, humectants will be used in amounts up to about 10 parts by weight.

Surfactants are often employed in therapeutic compositions to increase the penetrating effects of the therapeutic. The surfactants may be one or more of anionic, cationic, amphoteric or nonionic surface-active compounds. Suitable anionic emulsifiers are, for example, alkyl sulfonates, alkylaryl sulfonates, alkyl sulfates, sulfates of hydroxylalkanols, alkyl and alkylaryl disulfonates, sulfonated fatty acids, sulfates and phosphates of polyethyoxylated alkanols and alkylphenols, as well as esters of sulfosuccinic acid. Suitable cationic emulsifiers are, for example, alkyl quatenary ammonium salts, and alkyl quatenary phosphonium salts. One type of suitable non-ionic emulsifier is the addition product of 5 to 50 moles of ethylene oxide adducted to straight-chain and branched-chain alkanols with 6 to 22 carbon atoms, or to alkylphenols, higher fatty acids, higher fatty acid amines, or primary and secondary higher alkyl amines. Other suitable non-ionic emulsifiers are one or more block copolymers of propylene oxide with ethylene oxide. Preferred surfactants include fluorinated alkyl amphoterics or sodium dioctylsulfosuccinate. When present, the surfactant will be used in amounts of about 0.05 to 5.0 parts by weight.

One skilled in the art, having the knowledge of the present specification, will readily ascertain those applications in which the use of the inventive therapeutic compositions would be advantageous. Any conventional method of applying the therapeutics to the particular substrates may be employed. These methods are well known in the field of therapeutics.

Throughout this application, various publications have been referenced. The disclosures in these publications are incorporated herein by reference in order to describe more fully the state of the art.

Throughout this disclosure, applicant will suggest various theories or mechanisms by which applicant believe the components in the therapeutic compositions function together in an unexpected manner to provide unique treatments for proteinaceous substrates such as skin and hair. While applicant may offer various mechanisms to explain the present invention, applicant does not wish to be bound by theory. These theories are suggested to better understand the present invention but are not intended to limit the effective scope of the claims.

The present invention is further illustrated by the following examples which are presented for purposes of demonstrating, but not limiting, the preparation of the compounds and compositions of this invention.

EXAMPLES

Background

While the data in these experiments demonstrates the applicability of the present invention for modifying hair, other nucleophilic sites on other proteinaceous substrates may also undergo the same acylation chemistry. Thus for example, hair, wool, skin, leather, silk, fur, felt, and nails, which all have nucleophilic sites available either along the polypeptide backbone or on the amino terminus, would be expected to react with the water-soluble/dipersible reactive succinimide functionality. The relative concentrations of the basic amino acids (lysine, histidine, and arginine) those most likely to undergo acylation) found in hair, wool, silk, leather, skin, and nails, are set out below.

| Amino Acid | Hair | Wool | Silk | Leather | Skin | Nails |
|---|---|---|---|---|---|---|
| Lysine | 2.6–3.1 | 2.7 | 0.7 | 3.4–5.6 | 5.4–6.3 | 3.1 |
| Histidine | 0.8–1.1 | 1.1 | 0.4 | 0.7 | 2.2–2.4 | 1.0 |
| Arginine | 8.8–9.6 | 10.2 | 1.1 | 8.0–8.6 | 5.2–7.1 | 6.4 |

Preparation of a Neutral Water-soluble/dispersible Poly (succinimide)

To a 500 mL 3- or 4-necked round bottom flask equipped with an overhead mechanical stirrer, oil bath with temperature controller, nitrogen line and reflux condenser, was added DMSO. Twenty grams of poly(succinimide) (weight average molecular weight=4,500) was dried at 120° C. for at least 1 hour, then added to the DMSO to achieve a solution of 20% solids. The poly(succinimide) solution was stirred and heated until all polymer dissolved (usually around 50–55° C.), and 6.22 grams ethanolamine was added slowly to the reaction. The reaction was maintained at 60° C. with stirring, under nitrogen, overnight, and periodically titrated as above for free amine concentration. After completion, the reaction was allowed to cool to room temperature, and transferred to a separatory funnel.

The reaction mixture was slowly added dropwise to a large excess of ethyl acetate with vigorous mechanical stirring. The viscous precipitate was suspended in acetone, stirred and broken up by hand. A mechanical homogenizer was used to reduce the particle size of the product, which allowed better extraction of the DMSO from the polymer in acetone. The powdered and granular products were isolated by vacuum filtration and dried overnight at 60° C. The polymers were then ground using a mortar and pestle, resuspended in acetone, homogenized (if the particle size was still large), filtered and dried again.

Preparation of a Cationic Water-soluble/dispersible Poly (succinimide)

The general synthetic route for preparing a water-soluble/dispersible poly(succinimide) is described below. To a 500 mL 3- or 4-necked round bottom flask equipped with an overhead mechanical stirrer, oil bath with temperature controller, nitrogen line and reflux condenser, was added DMSO. Poly(succinimide) was dried at 120° C. for at least 1 hour, then added to the DMSO to achieve a solution of 20% solids. The poly(succinimide) solution was stirred and heated until all polymer dissolved (usually around 50–55° C.), and dimethyl amino propyl amine was added slowly to the reaction. The reaction was maintained at 60° C. with stirring, under nitrogen, overnight, and periodically titrated as above for free amine concentration.

After completion, the reaction was allowed to cool to room temperature, and transferred to a pressure reactor. The reaction mixture was exposed to CH₃Cl gas. The pressure in the reactor was measured and the reaction was allowed to proceed until the pressure no longer changes. The reactor was depressurized and the resulting solution was transferred to a separatory funnel.

The reaction mixture was slowly added dropwise to a large excess of ethyl acetate with vigorous mechanical stirring. The viscous precipitate was suspended in acetone, stirred and broken up by hand. A mechanical homogenizer was used to reduce the particle size of the product, which allowed better extraction of the DMSO from the polymer in acetone. The powdered and granular products were isolated by vacuum filtration and dried overnight at 60° C. The polymers were then ground using a mortar and pestle, resuspended in acetone, homogenized (if the particle size was still large), filtered and dried again.

Rate of Reaction of Water-soluble/dispersible Polysuccinimides with Nucleophilic Agents Versus Hydrolysis This example describes the reaction of a water-soluble/dispersible polysuccinimide with an organic amine in water to show that polysuccinimide can be made water-soluble/dispersible and that its rate of reaction with nucleophilic agents (an amine in this case) in aqueous media is competitive with that of the hydroysis reaction. The result is a level of acylating ability that allows modification of substrates in aqueous media. To prove that polysuccinimide (PSI) derivatives can react with amines in water to form covalent amide linkages, a study was conducted to determine reaction rates and rates of amidation versus hydrolysis. In the first series of experiments, the rate of hydrolysis (Scheme 1) of polysuccinimide derivatives at various pHs was measured by applying a pseudo-first order kinetics analysis (Scheme 1). The rate and extent of amidation versus hydrolysis was then measured by treating the polysuccinimide derivative with an amine in water (Scheme 2).

Scheme 1
Simple Hydrolysis

Fp38-40

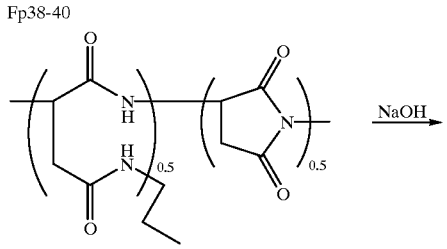

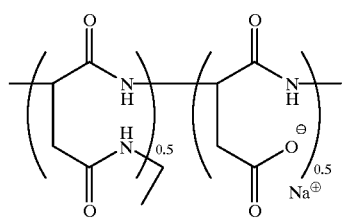

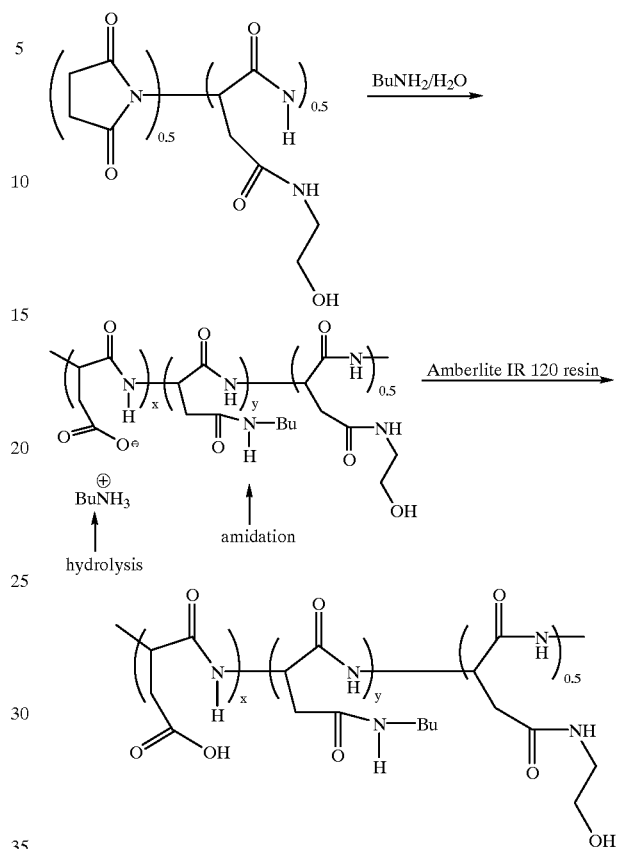

Amidation versus Hydrolysis

In the above studies, a polysuccinimide derivative that has been functionalized with 50 mol % of ethanolamine was used as a model material. The derivative is water-soluble/dispersible and has a simple, assignable NMR spectrum. For the amidation versus hydrolysis experiments, NMR was used to determine the ratio of amidation (value of "y" in Scheme 2) to hydrolysis (value of "x" in Scheme 2). The amine salt resulting from the hydrolysis reaction was removed via ion exchange, before NMR analysis was performed Hydrolysis of Reactive Derivatives Procedure Make a 1% aqueous solution of PSI derivative. Hold pH constant, using 1N sodium hydroxide, at desired pH using pH STAT method on Brinkman autotitrator. Monitor sodium hydroxide uptake. From the amount of sodium hydroxide used to open the succinimide rings, the rate of hydrolysis can be determined. Determine the amount of sodium hydroxide needed to hydrolyze the succinimide rings, and the rate at which hydrolysis occurs.

Pseudo-First Order Kinetic Analysis Results

| pH | Time to 25% Hydrolysis | Time to 50% Hydrolysis |
|---|---|---|
| 5.00 | No hydrolysis occurred after 3 days | — |
| 6.00 | 36.7 hours | — |
| 7.00 | 14.4 hours | — |
| 8.00 | 67 minutes | 7.8 hours |
| 9.00 | 9.5 minutes | 52.5 minutes |
| 10.00 | 2.25 minutes | 11.25 minutes |
| 11.00 | 2.0 minutes | 4.0 minutes |

As set out above, the reaction takes place very quickly at high pH.

Results:

| Expt.# | pH | PSI Actives (%) | Equivalents of Butylamine | # Amidations vs. # Hydrolysis |
|---|---|---|---|---|
| 1 | 5.00** | 5% | 3 | 1:14 |
| 2 | 9.00 | 0.9% | 3 | 1:17 |
| 3 | 10.00 | 1% | 3 | 1:94 |
| 4 | 10.00 | 10% | 1 | 1:7 |
| 5 | 10.00 | 10% | 3 | 1:7 |
| 6 | 11.00 | 1% | 3 | 1:24 |
| 7 | 11.00 | 10% | 3 | 1:1 to 1:6 |
| 8 | 11.45 | 4.5% | 3 | 1:1 to 1:3 |

General Conclusions

At pH 10–11, there is significant amidation which competes with hydrolysis. In fact, under certain conditions, 1 amidation event can occur for every 1 hydrolysis, that is, x=0.25 and y=0.25 in Scheme 2.

Time Experiment

Procedure

The general procedure is the same as that used for the Amidation versus Hydrolysis experiment except that samples are taken at designated times. Each sample is treated with two or more equivalents of ion-exchange resin. The resin is filtered off and the material is freeze-dried. An NMR is then taken of the product.

Results and Conclusions

The experiment was run at pH=10, 10% PSI actives, and 1 equivalent of butylamine and at pH=11, 10% PSI actives, and 3 equivalents of butylamine. At pH 10, the reaction is over after about thirty minutes and at pH 11, the reaction is over in about five minutes. Thus, at high pH reaction of the polysuccinimide (either hydrolysis or amidation) takes place extremely quickly.

Overall Conclusions

The above results demonstrate that under homogeneous conditions, amidation competes very favorably with hydrolysis at high pH, and that it is possible to form covalent amide linkages under aqueous conditions.

Modification of Hair With a Water-soluble/dispersible Polysuccinimide—Proof of Reaction One strategy to demonstrating covalent linkage between water-soluble/dispersible reactive derivative and proteinaceous substrate is to treat the proteinaceous substrate with polymer and measure the permanence of a change in the surface properties as a function of washing the surface with a good solvent for the polymer. The concept is that lack of covalent linkage allows polymer to be removed from the surface due to solubility in the solvent or conversely; that the presence of covalent linkage maintains the permanence of the effect as a function of successive washings.

A measurable property of the surface of hair is its ability to be wet by water. Instrumentation (KRUSS K14 Tensiometer) allows measurement of the force necessary to immerse a single fiber of hair into water. In this manner a relation between that force (Wetting Force) and contact angle between the water and the hair fiber can be used to detect changes which have been made to the surface of the hair. The following expression describes the relation between the Wetting Force (Fw) and the contact angle ($\phi$) of a solid cylinder of perimeter, p being immersed into a liquid with surface tension $\gamma$; Fw=p $\gamma$cos $\phi$.

It is well known that European, brown, virgin hair has, on average, a circular cross-section with perimeter 0.221 mm, therefore allowing approximation to a solid cylinder. It is furthermore well known that the surface of European, brown, virgin, hair is hydrophobic. This means that the contact angle of water on the surface of hair is greater than or equal to 90°. This then corresponds to a near zero or negative wetting force (as $\phi \rightarrow 90°$, cos $\phi \rightarrow 0$, as cos $\phi \rightarrow 0$, Fw$\rightarrow 0$).

Addition of a layer of water-soluble/dispersible poly (succinimide), bound to the surface of European, brown, virgin, hair will decrease the hydrophobicity of hair due to the addition of functional groups such as aspartic acid and hydroxyethyl aspartamide. A decrease in the hydrophobicity of hair will allow water to wet the surface of hair better. Subsequently, the contact angle $\phi$ will be reduced. A reduction in contact angle corresponds to an increase in wetting force. Subsequently, the contact angle $\phi$ will be reduced. A reduction in contact angle corresponds to an increase in wetting force.

The change in the hydrophobicity of virgin hair due to the presence of polar and hydrogen bonding units of the reactive polymer can be used as a measure of the presence of the reactive polymer on hair. Measurement of this property as a function of washes in a known good solvent (detergent solution) for the polymer will allow conclusions about the permanence of the effect.

Hair treatment with water-soluble/dispersible poly (succinimide) of polysuccinimide can generally be viewed as having two steps. In the first step, hair is treated with reactive derivative in order to deposit the derivative onto or into the hair. In the second step, hair treated with reactive derivative is exposed to conditions that favor the deprotonation of nucleophilic groups on the surface of hair such as amine and sulfhydryl that are expected to be present due to the amino acid composition of hair keratin. These nucleophilic species are then capable of reacting with succinimide moieties on the polymer and covalently linking the surface of hair to the polymer. The following diagram schematically depicts the process.

Plot 1

Schematic of Hair Treatment with Water-soluble Reactive Derivative of Polysuccinimide

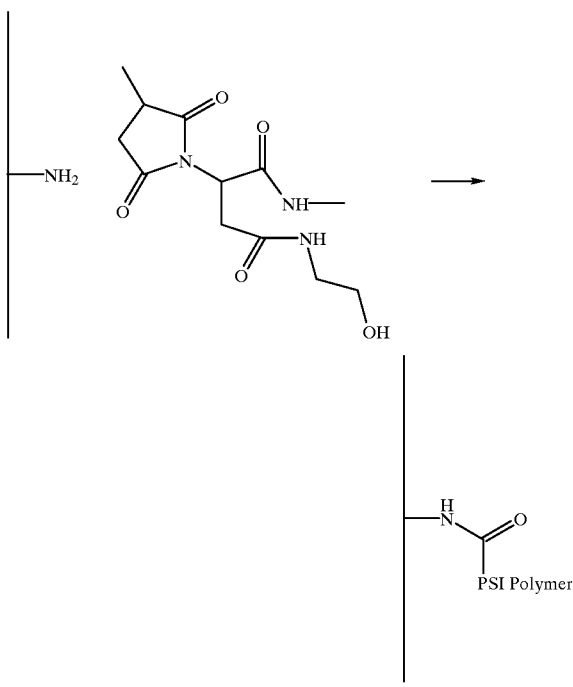

PSI Polymer

The following experimental design employs the wetting force measurement strategy and comparative experiments to demonstrate the concept of covalent linkage of the polymer to hair.

In the first step, the hair fibers (in the form of a 0.5 gram bundle of hair of approximately 12 inch in length) were rinsed with chloroform followed by methanol then chloroform. This solvent rinse is designed to remove polar and non-polar impurities. Following this rinse, the hair was immersed in a pH=7 buffer solution (0.2N $Na_2HPO_4$/0.1N Citric Acid). The hair was then rinsed in deionized water and dried. Tresses 11A and 11B were then immersed into a 10% (mass) solution of water-soluble/dispersible poly (succinimide) (50% (mole) imide/50%(mole) ethanolamine) with weight average molecular weight of 4500. Tress 11C was treated with a hydrolyzed (non-reactive) version of the same polysuccinimide. Tress 11, 11B, and 11C were then immersed into 30 mL of pH=10 buffer solution (0.02N sodium carbonate/sodium bicarbonate) and heated to 50° C. for 60 minutes. Tress 11A was immersed into 30 mL of deionized water and heated to 50° C. for 60 minutes.

Following these treatments, the hair was washed with water five times followed by 20 washes in a 3%(mass) solution of triethanolamine lauryl sulfate. The hair tress was immersed in the washing solution and excess solution was squeezed out after each immersion. Several hair fibers were randomly selected for wetting force testing.

Tress 11 is a control tress to determine the effect of the process conditions on the surface of hair. Tress 11A is treated in a manner to determine if permanent changes in the surface properties of hair are observed with treatment conditions that do not favor reaction between the polymer and hair. Tress 11B is treated in a manner to favor the reaction. Tress 11C is treated with a non-reactive version of the polysuccinimide used in 11A and 11B.

The wetting force of the treated hair did not vary with immersion depth. Therefore, the wetting force results are presented as the average value over the immersion depth. Table 1 tabulates the results after 20 detergent washes.

TABLE 1

Average Wetting Force After 20 Detergent Washes

| Tress# | Wetting Force |
|---|---|
| 11 | 0.000148 |
| 11A | 0.000110 |
| 11B | 0.000644 |
| 11C | 0.000174 |

The results of the wetting force measurements clearly show that only tress 11B demonstrates a permanent increase in wetting force after detergent washes. The fact that tress 11 did not display an increase in wetting force indicates the effect was not caused by process conditions. The fact that tress 11C did not display an increase in wetting force indicates the effect was not caused by non-covalent binding between hair and polymer. The fact that tress 11B, which was not exposed to conditions favoring acylation did not display a permanent increase in wetting force and that 11A did (see favorable reactions) suggests that covalent linkage occurs between the polymer and hair.

Internal Modification of Damaged Hair Using Water-soluble/dispersible Polysuccinimides Hair that has been bleached and/or permed is chemically damaged. The chemical damage is the result of cleavage of the sulfur-sulfur cross-linkages and alkaline cleavage of amide linkages in the protein chains of the hair which frequently fail to reform completely. As a result, hair is weakened. The strength or weakness of the hair can be measured as a function of its ability to withstand stretching to an additional 20% of its original length, i.e. damaged hair is relatively easy to extend 20% whereas intact hair requires much more work to extend an additional 20%. In this experiment, the extent to which the strength of chemically damaged (bleach/perm) hair can be rebuilt was measured. Hair strength was measured by measuring the work required to extend the hair an additional 20% of its length.

Four polymers were prepared with the compositions set out below. The molecular weights of the starting poly (succinimide) were 1100, 2500, and 4500. Each molecular weight was derivatized with 50 mole % ethanolamine. Additionally, the Mw=2500 starting poly(succinimide) was derivatized with 50 mole % DMAPA (Cl-quat). There were three treatment conditions studied: 1) 60 minute soak of hair in polymer solution followed by a soak in a pH=10 buffer solution, at 45° C., for 30 minutes, 2) 60 minute soak of bleached, permed hair in polymer solution followed by soak in a solution of poly(ethyleneimine) Mw=750,000 (5% by mass, pH=10.8), at 45° C., 30 minutes, 3) 60 minute soak of hair in polymer solution followed by a soak in a solution of hexamethylene diamine, at 45° C., for 30 minutes. Additionally, three concentrations of hexamethylene diamine were tested: 0.22%, 2.2%, and 4.4% (mass %, pH=10–11.5). Control experiments were performed for each different process. These control experiments consisted of substitution of the polymer treatment with a 60 minute soak in pH=5.4 buffer (pH of water-soluble/dispersible-reactive derivative) followed by the identical treatment as described in 1), 2), and 3) above.

TABLE 1a

Composition of Reparative Polymers

| Mol. Wt | Water-solubilizing Group | % Water-solubilizing Group (mole %) | % Imide (mole %) |
|---|---|---|---|
| 1100 | Ethanolamine | 50 | 50 |
| 2500 | Ethanolamine | 50 | 50 |
| 4500 | Ethanolamine | 50 | 50 |
| 2500 | DMAPA Quat | 50 | 50 |

Results

Table 1a defines the legend for the figure, tabulates the data, and the 20% index. The 20% index is defined as the ratio of the work to 20% extension after treatment to the work to 20% extension before treatment. The work to 20% extension before treatment is taken as the value for bleach/perm hair.

Table 2 tabulates the data and the 20% index

TABLE 2

| Treatment | Average Work to 20% Extension (Gm cm) | Standard Deviation (Gm cm) | 20% Index |
|---|---|---|---|
| A Virgin Brown Hair | 95.9 | — | — |
| B Bleached/Permed Hair | 42.3 | — | 1 |
| C B + Buffer Process Control | 42.6 | 26.7 | 1.007 |
| D B + Mw = 1100 Neutral | 64.7 | 29.2 | 1.529 |
| E B + Mw = 2500 Neutral | 58.2 | 29 | 1.375 |
| F B + Mw = 2500 Cationic | 45.4 | 23.6 | 1.075 |
| G B + Mw = 4500 Neutral | 41.7 | 24.8 | 0.9858 |

Comparison of A and B demonstrates the well-known degradation of tensile properties of hair upon chemical processing. Comparison of B and C demonstrates that the buffer treatment process has no impact on the tensile properties of damaged hair. Comparison between D, E, and G show the relation between performance and molecular weight. Comparisons of E and F show the impact of a cationic charge. The neutral material (E) shows a 20% Index significantly>1 while the cationic one (F) shows a 20% index only slightly>1.

These data allow the following conclusions. In order to be effective in improving the strength of damaged hair, the polymers should have a molecular weight<4500. Optimally the polymer should have a molecular weight in the range 1100–2500. The polymer should not be cationic in charge.

Table 3 tabulates the data, and the 20% index.

TABLE 3

| Treatment | Average Work to 20% Extension (Gm cm) | Standard Deviation (Gm cm) | 20% Index |
|---|---|---|---|
| A Virgin Brown Hair | 95.9 | — | — |
| B Bleached/Permed Hair | 42.3 | — | 1 |
| H PEI Control | 69.5 | 33 | 1.64 |
| I Mw = 2500 Neutral PEI | 69.4 | 34.8 | 1.64 |
| J HMD Control | 53.7 | 25.2 | 1.26 |
| K Mw = 2500 Neutral mid HMD | 95.8 | 41.4 | 2.26 |
| L Mw = 1100 Neutral mid HMD | 89.7 | 44 | 2.12 |
| M Mw = 4500 Neutral mid HMD | 52.7 | 42 | 1.24 |
| N Mw = 2500 Neutral low HMD | 58.9 | 32 | 1.39 |
| O Mw = 2500 Neutral High HMD | 68.4 | 20 | 1.61 |

Comparison between B and H demonstrates that control treatment with poly(ethyleneimine) Mw=750000 shows a positive impact on the work to 20% extension. Comparison between H and I shows no benefit to the addition of the water-soluble/dispersible reactive derivative. Comparison between B and J demonstrates that the control treatment with hexamethylene diamine shows a positive impact on the work to 20% extension. However addition of the water-soluble/dispersible reactive derivative of poly(succinimide) shows a dramatic improvement over this control. Comparison between K, L, and M again demonstrates the performance as a function of molecular weight. Comparisons between K, N, and O demonstrate that there is an optimum concentration of hexamethylene diamine.

These data allow the following conclusions. There is a benefit in a reaction step employing a multifunctional amine. The multifunctional amine should be low in molecular weight. There is an optimum concentration of the multifunctional amine. The polymer should have molecular weight<4500. Optimally the polymer should have a molecular weight in the range 1100–2500.

The Use of the Primer Approach to Impart Conditioning to Hair

It is well known that chemically processed hair (bleach/perm) suffers from poor wet combability. Poor wet combability results in an unpleasant combing experience and often times to hair breakage. Combing aids historically employed cationic surfactants and cationic polymers. The aids are substantive to hair and provide an improvement in wet combability. Currently hair care products employing these ingredients suffer from build up problems upon repeated use that result in undesirable aesthetics. Furthermore, the conditioning afforded by these products is only temporary. In the example below, a more durable approach to conditioning hair that affords controlled deposition of the conditioning aid (and thus eliminates the potential for build-up) is described.

Four polymers were applied to hair. Table 4 describes the composition of these polymers. Polymers #1 and #2 are water soluble/dispersible poly(succinimide)s having varying levels of cationic substitution (tri-methyl amino propyl amine). Polymer #3 is a non-reactive version of polymer #1 and has no group capable of covalent linkage to hair. Polymer #4 is a cationic hydroxyethyl cellulose derivative (Polyquaternium 10) used as a wet comb aid.

TABLE 4

Polymers Used in Wet Combability Study

| Name | Backbone | Attractive/Binding Group | Reactive Group |
|---|---|---|---|
| #1 | PSI | 80% | 20% |
| #2 | PSI | 40% | 60% |
| #3 | PSI | 80% | 0% |
| #4 | HEC | Polyquaternium 10 | — |

Ease of wet combing is viewed as an indication of conditioned hair. The experiment was designed to determine the wet combability of hair after treatment with the polymer as a function of 10% sodium lauryl sulfate (aq) solution. The % original work of wet comb is calculated by dividing the work of wet comb after polymer treatment and washing by the work of wet comb before polymer treatment and multiplying the result by 100. Hence, a lower % indicates an improvement in wet combability. Table 5 tabulates the results.

TABLE 5

Tabulated Wet Combability Results

| # of Washes | #Control | #1 | #2 | #3 | #4 |
|---|---|---|---|---|---|
| 0 | 100 | 100 | 100 | 100 | 100 |
| 1 | — | — | — | 30 | 65 |
| 4 | 89 | 46 | 40 | — | — |
| 5 | — | — | — | 60 | 110 |
| 9 | — | — | — | 85 | 112 |
| 10 | — | 59 | 42 | — | — |
| 15 | 102 | 38 | 29 | — | — |
| 20 | 84 | 44 | 42 | — | — |

The experiment was designed to determine the wet compatibility of hair after treatment with these polymers in #4 as a function of washing in a 10% sodium lauryl sulfate solution. A plot is prepared of % of original work of wet comb versus the number of washes in 10% SLS solution. The % original work of wet comb is calculated by dividing the work of wet comb after polymer treatment and washing to the work of wet comb before polymer treatment and multiplying the result by 100. Hence a lower % demonstrates a reduction in wet combability.

The control result is the result of bleach/perm damaged hair which was subjected to acylation conditions (e.g., time, temperature, pH, washes, etc.) but which never came in contact with a water-soluble reactive derivative. The control shows no significant reduction in over 20 washes.

Polyquaternium 10 (cationic hydroxyethyl cellulose) is a polymer currently used as a hair conditioning polymer. It is cationic and thus substantive to hair, however, it has no group capable of forming a covalent bond to hair. The results for Polyquaternium 10 shows an initial significant reduction in wet combability followed by a steady 'give back' to the level of the control after 10 washes.

The results for polymer #3 show a similar trend. Polymer #3 is also cationic and thus substantive to hair and again it has no group capable of binding to hair. It exhibits similar behavior to Polyquaternium 10 in that it shows an initial reduction in wet combability followed by a 'give back' after a few washes.

Polymers #1 and #2 show similar behavior in that they show a reduction in wet combability and maintain that reduction as a function of washing as long as twenty washes. Both polymers display nearly identical performance.

The results demonstrate the following. First, polymers without covalent binding groups give a transient improvement in wet combability. This is most likely because the ionic bond between anionic hair and cationic polymer are solvent sensitive and can be affected by aqueous surfactant. Second, binding a cationic polymer to hair and using it to attract anionic surfactant gives significant improvements in wet combability that is more durable than traditional approaches. Furthermore, because the cationic groups of the polymer are the only groups capable of binding the active species (anionic surfactant), the deposition of the active is controlled and there is no opportunity for build up.

While a number of embodiments of this invention have been represented, it is apparent that the basic construction can be altered to provide other embodiments which utilize the invention without departing from the spirit and scope of the invention. All such modifications and variations are intended to be included within the scope of the invention as defined in the appended claims rather than the specific embodiments which have been presented by way of example.

We claim:

1. A polyimido compound selected from the group consisting of polysuccinimide compounds represented by Formula (1):

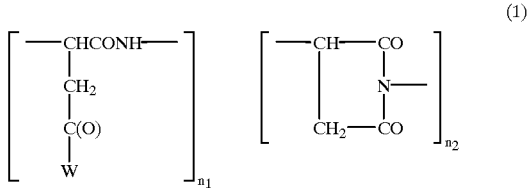

polyglutimide compounds represented by Formula (2);

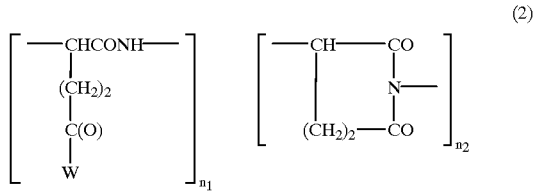

and copolymers of the polysuccinimide compounds represented by Formula (1) with the polyglutimide compounds represented by Formula (2); wherein W is a water-solubilizing/dispersing moiety that provides water-solubility and/or water-dispersibility to the polyimido compound, wherein W is selected from the group consisting of:

(1) aminopolysaccharides represented by the formula, $-N(R_1)$-polysaccharide, wherein $R_1$ is hydrogen or lower alkyl and the number of units in the polysaccharide ranges from 1 to about 51;

(2) amines containing quatenary ammonium salts represented by the formula, $[-N(R_1)(CH_2)_{n3}N^+(CH_3)_3]$ $[A^-]$, wherein $R_1$ is hydrogen or lower alkyl, $n_3$ is an integer from 1 to about 10, and A is a monovalent anion;

(3) amines containing alcohols represented by the formula, $-N(R_1)(CH_2)_{n4}OH$, wherein $R_1$ is hydrogen or lower alkyl and $n_4$ is an integer from 2 to about 10;

(4) amines containing polyalkoxylated alcohols represented by the formula, $-N(R_1)CH(CH_3)CH_2-$ $(OCHR_2CH_2)_{n5}-OCH_3$, wherein $R_1$ is hydrogen or lower alkyl, $R_2$ may be hydrogen or methyl, and $n_5$ is an integer from 0 to about 50;

(5) thiols containing alcohols represented by the formula, $-S(CH_2)_{n6}OH$, wherein $n_6$ is an integer ranging from 2 to about 10;

(6) alcohols containing ethers represented by the formula, $-O(CH_2CH_2)_{n7}OM$, wherein $n_7$ is an integer ranging from 0 to about 50 and M is an alkyl group containing from 1 to about 30 carbons; and (7) $-O^-X^+$, where X is selected from the group consisting of $H^+$, $Na^+$, $Li^+$, $NH_4^+$, $NH(CH_3)_3^+$, $NH_3(CH_2CH_2OH)^+$, $NH_2(CH_2CH_2OH)_2^+$, and $NH(CH_2CH_2OH)_3^{\pm}$;

with the proviso that $n_1 \neq n_2$ when W is selected from the group consisting of $H^+$, $Na^+$, $Li^+$, $NH_4^+$, $NH(CH_3)_3^{30}$, $NH_3(CH_2CH_2OH)^+$, $NH_2(CH_2CH_2OH)_2^+$, and $NH(CH_2CH_2OH)_3^{\pm}$ the ratio of $n_1$ to $n_2$ is from about 1:99 to about 99:1; and the molecular weight of the polyimido compound is from about 300 to about 1,000,000.

2. The polyimido compound according to claim 1, wherein the ratio of $n_1$ to $n_2$ is from about 95:5 to about 5:95.

3. The polyimido compound according to claim 1, wherein the molecular weight of the polyimido compound is from about 300 to about 5000.

4. The polyimido compound according to claim 1, wherein the molecular weight of the polyimido compound is greater than about 5000.

5. The polyimido compound according to claim 1, wherein the polyimido compound is a polysuccinimide represented by Formula (1).

6. The polyimido compound according to claim 1, wherein the polyimido compound is a polyglutimide represented by Formula (2).

7. The polyimido compound according to claim 1, wherein the polyimido compound is a copolymer of the polysuccinimide represented by Formula (1) with the polyglutimide represented by Formula (2).

8. The polyimido compound according to claim 1, further comprising a pharmaceutically acceptable carrier.

9. A proteinaceous substrate, having a polyimido compound covalently bonded to a portion thereof, wherein the polyimido compound is selected from the group consisting of polysuccinimide compounds represented by Formula (1):

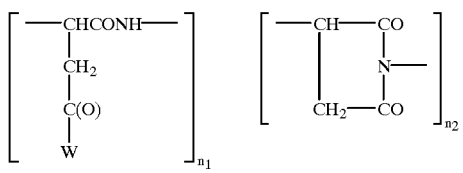

(1)

polyglutimide compounds represented by Formula (2);

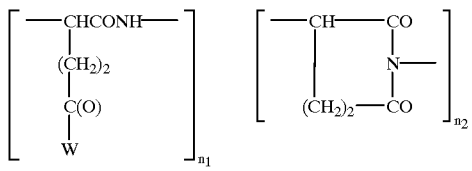

(2)

and copolymers of the polysuccinimide compounds represented by Formula (1) with the polyglutimide compounds represented by Formula (2); wherein W is a water-solubilizing/dispersing moiety that provides water-solubility and/or water-dispersibility to the polyimido compound; the ratio of $n_1$ to $n_2$ is from about 1:99 to about 99:1; and the molecular weight of the polyimido compound is from about 300 to about 1,000,000.

10. The proteinaceous substrate according to claim 9, wherein W is derived from a nucleophilic moiety selected from the group consisting of amines, alcohols, phenols, thiols, and carboxylates.

11. The proteinaceous substrate according to claim 10, wherein W is selected from the group consisting of:

(1) aminopolysaccharides represented by the formula, —N($R_1$)-polysaccharide, wherein $R_1$ is hydrogen or lower alkyl and the number of units in the polysaccharide ranges from 1 to about 51;

(2) amines containing quatenary ammonium salts represented by the formula, [—N($R_1$)($CH_2$)$_{n3}$N$^+$($CH_3$)$_3$][A$^-$], wherein $R_1$ is hydrogen or lower alkyl, $n_3$ is an integer from 1 to about 10, and A is a monovalent anion;

(3) amines containing alcohols represented by the formula, —N($R_1$)($CH_2$)$_{n4}$OH, wherein $R_1$ is hydrogen or lower alkyl and $n_4$ is an integer from 2 to about 10;

(4) amines containing polyalkoxylated alcohols represented by the formula, —N($R_1$)CH($CH_3$)$CH_2$—(OCH$R_2$$CH_2$)$_{n5}$—OCH$_3$, wherein $R_1$ is hydrogen or lower alkyl, $R_2$ may be hydrogen or methyl, and $n_5$ is an integer from 0 to about 50;

(5) thiols containing alcohols represented by the formula, —S($CH_2$)$_{n6}$OH, wherein $n_6$ is an integer ranging from 2 to about 10;

(6) alcohols containing ethers represented by the formula, —O($CH_2CH_2O$)$_{n7}$OM, wherein $n_7$ is an integer ranging from 0 to about 50 and M is an alkyl group containing from 1 to about 30 carbons;

(7) —O$^-$X$^+$, where X is selected from the group consisting of H$^+$, Na$^+$, Li$^+$, NH$_4^+$, NH(CH$_3$)$_3^+$; NH$_3$(CH$_2$CH$_2$OH)$^+$, NH$_2$(CH$_2$CH$_2$OH)$_2^+$, and NH(CH$_2$CH$_2$OH)$_3^+$; and (8) [—NH(CH$_2$)$_3$N$^+$(CH$_3$)$_2$CH$_2$COONa][A$^-$], —N(CH$_3$)(CH$_2$)$_2$SO$_3$Na, and —NH(CH$_2$)$_2$SO$_3$Na, wherein A is a monovalent anion.

12. The proteinaceous substrate according to claim 9, wherein the ratio of $n_1$ to $n_2$ is from about 95:5 to about 5:95.

13. The proteinaceous substrate according to claim 9, wherein the molecular weight of the polyimido compound is from about 300 to about 5000.

14. The proteinaceous substrate according to claim 9, wherein the molecular weight of the polyimido compound is greater than about 5000.

15. The proteinaceous substrate according to claim 9, wherein the polyimido compound is a polysuccinimide represented by Formula (1).

16. The proteinaceous substrate according to claim 9, wherein the polyimido compound is a polyglutimide represented by Formula (2).

17. The proteinaceous substrate according to claim 9, wherein the polyimido compound is a copolymer of the polysuccinimide represented by Formula (1) with the polyglutimide represented by Formula (2).

18. The proteinaceous substrate according to claim 9, wherein the proteinaceous substrate is selected from the group consisting of hair, wool, skin, leather, silk, fur, felt, and nails.

19. The proteinaceous substrate according to claim 9, wherein the polyimido compound is cross-linked to a multifunctional nucleophilic agent.

20. The proteinaceous substrate according to claim 19, wherein the multifunctional nucleophilic agent is selected from the group consisting of 1,6-hexamethylenediamine, low-molecular weight polyethyleneimines, polyalkoxides, and polythiols.

21. The proteinaceous substrate according to claim 9, wherein the water-solubilizing/dispersing moiety bears an ionic charge and is electrostatically bound to a moiety bearing the opposite charge.

22. The proteinaceous substrate according to claim 21, wherein the moiety bearing the opposite charge is selected from the group consisting of antimicrobials, ultraviolet chromophores, anionic dyes, anti-oxidants, fluorescing agents, brightening agents, shine and gloss enhancers, softening agents, and conditioning agents.

23. A method for treating a proteinaceous substrate which comprises the steps of:

(a) contacting a proteinaceous substrate with an aqueous solution/dispersion of an imido or polyimido compound at a pH value between about 4 and about 7 for a time sufficient to allow the imido or polyimido compound to be adsorbed/absorbed on or into the proteinaceous substrate; and (b) raising the pH value of the imido or polyimido compound adsorbed/absorbed on or into the proteinaceous substrate above about 7 for a time sufficient to allow the imido or polyimido compound to covalently bond with the proteinaceous substrate.

24. A method for treating a proteinaceous substrate which comprises the steps of:

(a) contacting a proteinaceous substrate with an aqueous solution of a polyimido compound at a pH value between about 4 and about 7 for a time sufficient to allow the polyimido compound to be adsorbed/absorbed on or into the proteinaceous substrate; and (b) raising the pH value of the polyimido compound adsorbed/absorbed on or into the proteinaceous substrate above about 7 for a time sufficient to allow the polyimido compound to covalently bond with the proteinaceous substrate; wherein the polyimido compound is selected from the group consisting of polysuccinimide compounds represented by Formula (1):

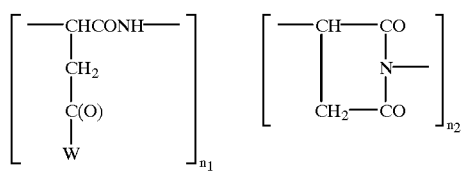

(1)

polyglutimide compounds represented by Formula (2);

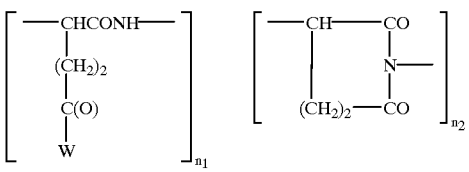

(2)

and copolymers of the polysuccinimide compounds represented by Formula (1) with the polyglutimide compounds represented by Formula (2); wherein W is a water-solubilizing/dispersing moiety that provides water-solubility and/or water-dispersibility to the polyimido compound; the ratio of $n_1$ to $n_2$ is from about 1:99 to about 99:1; and the molecular weight of the polyimido compound is from about 300 to about 1,000,000.

25. The method according to claim 24, wherein W is derived from a nucleophilic moiety selected from the group consisting of amines, alcohols, phenols, thiols, and carboxylates.

26. The method according to claim 25, wherein W is selected from the group consisting of:

(1) aminopolysaccharides represented by the formula, —N($R_1$)-polysaccharide, wherein $R_1$ is hydrogen or lower alkyl and the number of units in the polysaccharide ranges from 1 to about 51;

(2) amines containing quaternary ammonium salts represented by the formula, [—N($R_1$)($CH_2$)$_{n3}$N$^+$($CH_3$)$_3$][A$^-$], wherein $R_1$ is hydrogen or lower alkyl, $n_3$ is an integer from 1 to about 10, and A is a monovalent anion;

(3) amines containing alcohols represented by the formula, —N($R_1$)($CH_2$)$_{n4}$OH, wherein $R_1$ is hydrogen or lower alkyl and $n_4$ is an integer from 2 to about 10;

(4) amines containing polyalkoxylated alcohols represented by the formula, —N($R_1$)CH($CH_3$)$CH_2$—(OCHR$_2$CH$_2$)$_{n5}$—OCH$_3$, wherein $R_1$ is hydrogen or lower alkyl, $R_2$ may be hydrogen or methyl, and $n_5$ is an integer from 0 to about 50;

(5) thiols containing alcohols represented by the formula, —S($CH_2$)$_{n6}$OH, wherein $n_6$ is an integer ranging from 2 to about 10;

(6) alcohols containing ethers represented by the formula, —O($CH_2CH_2O$)$_{n7}$OM, wherein $n_7$ is an integer ranging from 0 to about 50 and M is an alkyl group containing from 1 to about 30 carbons;

(7) —O$^-$X$^+$, where X is selected from the group consisting of H$^+$, Na$^+$, Li$^+$, NH$_4^+$, NH(CH$_3$)$_{3+}$; NH$_3$(CH$_2$CH$_2$OH)$^+$, NH$_2$(CH$_2$CH$_2$OH)$_2^+$, and NH(CH$_2$CH$_2$OH)$_3^+$; and (8) [—NH(CH$_2$)$_3$N$^+$(CH$_3$)$_2$CH$_2$COONa][A$^-$], —N(CH$_3$)(CH$_2$)$_2$SO$_3$Na, and —NH(CH$_2$)$_2$SO$_3$Na, wherein A is a monovalent anion.

27. The method according to claim 24, wherein the ratio of $n_1$ to $n_2$ is from about 95:5 to about 5:95.

28. The method according to claim 24, wherein the molecular weight of the polyimido compound is from about 300 to about 5000.

29. The method according to claim 24, wherein the molecular weight of the polyimido compound is greater than about 5000.

30. The method according to claim 24, wherein the polyimido compound is a polysuccinimide represented by Formula (1).

31. The method according to claim 24, wherein the polyimido compound is a polyglutimide represented by Formula (2).

32. The method according to claim 24, wherein the polyimido compound is a copolymer of the polysuccinimide represented by Formula (1) with the polyglutimide represented by Formula (2).

33. The method according to claim 24, wherein the proteinaceous substrate is selected from the group consisting of hair, wool, skin, leather, silk, fur, felt, and nails.

34. The method according to claim 24, wherein the polyimido compound is cross-linked to a multifunctional nucleophilic agent.

35. The method according to claim 34, wherein the multifunctional nucleophilic agent is selected from the group consisting of 1,6-hexamethylenediamine, low-molecular weight polyethyleneimines, polyalkoxides, and polythiols.

36. The method according to claim 24, wherein the water-solubilizing/dispersing moiety bears an ionic charge and is electrostatically bound to a moiety bearing the opposite charge.

37. The method according to claim 36, wherein the moiety bearing the opposite charge is selected from the group consisting of antimicrobials, ultraviolet chromophores, anionic dyes, anti-oxidants, fluorescing agents, brightening agents, shine and gloss enhancers, softening agents, and conditioning agents.

* * * * *